United States Patent [19]

Primeau et al.

[11] Patent Number: 5,234,936

[45] Date of Patent: Aug. 10, 1993

[54] PYRIMIDOCYCLOALKANES AS A II ANTAGONISTS

[75] Inventors: John L. Primeau, Princeton; Lloyd M. Garrick, Plainsboro; Timothy D. Ocain, Princeton; Richard M. Soll, Lawrenceville, all of N.J.; Paul J. Dollings, Newtown, Pa.

[73] Assignee: American Home Products Corporation, New York, N.Y.

[21] Appl. No.: 782,017

[22] Filed: Oct. 24, 1991

[51] Int. Cl.$^5$ .................. C07D 239/72; C07D 239/86; C07D 239/94

[52] U.S. Cl. ..................................... 514/259; 514/260; 544/253; 544/283; 544/284; 544/286; 544/291; 544/292; 544/293; 544/295

[58] Field of Search ............... 544/253, 284, 286, 291, 544/292, 293, 283; 514/259, 260

[56] References Cited

U.S. PATENT DOCUMENTS

| | | | |
|---|---|---|---|
| 4,450,162 | 5/1984 | Kamioka et al. | 514/259 |
| 4,464,375 | 8/1984 | Kobayashi et al. | 514/259 |
| 4,749,704 | 6/1988 | Iwata et al. | 514/258 |
| 4,880,804 | 11/1989 | Carini et al. | 514/234.5 |

FOREIGN PATENT DOCUMENTS

| | | |
|---|---|---|
| 0401030 | 12/1990 | European Pat. Off. . |
| 0411766 | 2/1991 | European Pat. Off. . |
| 0412848 | 2/1991 | European Pat. Off. . |
| 0419048 | 3/1991 | European Pat. Off. . |
| 0424317 | 4/1991 | European Pat. Off. . |

OTHER PUBLICATIONS

Chiu et al., European Journal of Pharmacology, 157(1988) 13-21.

Primary Examiner—Mukund J. Shah
Assistant Examiner—Matthew V. Grumbling
Attorney, Agent, or Firm—Walter Patton

[57] ABSTRACT

There are disclosed compounds of the general formula I:

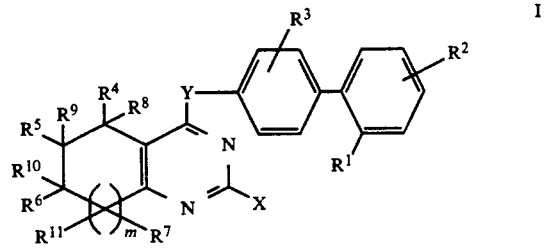

wherein
X is H, $NR^{12}R^{13}$, $OR^{14}$, CN, F, Cl, I, Br, perfluoroalkyl, alkyl, alkoxy, alkyl-OH, alkoxyalkyl, $-(CH_2)_nCO_2R^{14}$, $-(CH_2)_nCONR^{12}R^{13}$;
Y is $NR^{15}$, $NR^{18}CR^{16}R^{17}$, $CR^{16}R^{17}NR^{15}$;
$R^1$ is 5-tetrazolyl, $CO_2R^{14}$, $SO_3H$, $NHSO_2CH_3$, $NHSO_2CF_3$;
$R^2$, $R^3$ is H, alkyl, alkoxy, alkoxyalkyl, alkyl-OH perfluoroalkyl, aralkyl, CN, $NO_2$, $SO_2R^{19}$, $-(CH_2)_nCO_2R^{14}$, $-(CH_2)_nCONR^{12}R^{13}$, $OR^{14}$, F, Cl, Br, I, $NR^{12}R^{13}$;
$R^4$-$R^{11}$ is H, F, alkyl, alkoxy, alkoxyalkyl, $-OCOR^{14}$, alkyl-OH, perfluoroalkyl, aralkyl, aryl, CN, $NO_2$, $SO_2R^{19}$, $-(CH_2)_nCO_2R^{14}$, $-(CH_2)_nCONR^{12}R^{13}$, OH, $OR^{14}$, $-NR^{12}R^{13}$, any two geminal groups can be O or $CH_2$;
$R^{12}$, $R^{13}$ is H, alkyl, aralkyl;
$R^{14}$ is H, alkyl, aralkyl, alkoxyalkyl;
$R^{15}$ is H, alkyl, $-(CH_2)_nCO_2R^{14}$, alkoxyalkyl, aralkyl, $-(CH_2)_nCONR^{12}R^{13}$, $OR^{14}$, perfluoroalkyl, alkyl-OH, $-COR^{14}$, $-CONR^{12}R^{13}$;
$R^{16}$, $R^{17}$ is H, alkyl, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$;
$R^{18}$ is H, alkoxyalkyl, alkyl-OH, perfluoroalkyl, aralkyl, $OR^{14}$, $-(CH_2)_nCO_2R^{14}$, $-(CH_2)_nCONR^{12}R^{13}$, alkyl, $-COR^{14}$, $-CONR^{12}R^{13}$;
$R^{19}$ is alkyl, aralkyl;
n is 0, 1, 2 or 3;
m is 1-5;

wherein alkyl is defined as 1-8 carbons, branched or straight chain; perfluoroalkyl is defined as 1-6 carbons; aralkyl is defined as 7-12 carbons or 7-12 carbons sub- (Abstract continued on next page.)

ABSTRACT stituted with fluorine, bromine or chlorine; aryl is defined as 6–10 carbons or 6–10 carbons substituted with fluorine, bromine or chlorine and the pharmaceutically acceptable salts, solvates and hydrates thereof, which by virtue of their ability to antagonize angiotensin II are useful for the treatment of hypertension and congestive heart-failure. The compounds are also useful for reducing lipid levels in the blood plasma and are thus useful for treating hyperlipidemia and hypercholesterolemia. Also disclosed are processes for the production of said compounds and pharmaceutical compositions containing said compounds.

30 Claims, No Drawings

PYRIMIDOCYCLOALKANES AS A II ANTAGONISTS

BACKGROUND OF INVENTION

The compounds described in this invention as well as their non-toxic salts and pharmaceutical compositions containing them are useful for the treatment of hypertension and congestive heart failure. These compounds are also useful as lipid lowering agents.

The renin-angiotensin system plays a well-defined role in cardiovascular homeostasis [Ocain, T. D. et al. (1991) Drugs of the Future 16, 37–51]. Angiotensinogen is converted to angiotensin I by the enzyme renin. Angiotensin I is then acted upon by angiotensin converting enzyme (ACE) to form angiotensin II (A II). A II possesses many crucial properties including vasoconstriction, aldosterone release, and water retention and is implicated as the cause of high blood pressure in a number of species including man. These hypertensive responses are the result of A II acting at specific receptor sites. Compounds which are able to compete with A II for these receptor sites but do not elicit agonistic receptor responses can be expected to counteract (antagonize) the hypertensive effects of A II.

PRIOR ART

E. E. Allen et al describe 4-oxo-quinazolines in EP 0411766 A.

D. A. Roberts et al describe quinoline ethers in EP 0412848 A.

D. J. Carini et al describe N-substituted benzimidaloles in U.S. Pat. No. 4,880,804. P. Chakravarty et al disclose similar imidazole structures in EP 0401030 A where the phenyl aromatic ring is replaced by a seven membered heterocycle.

E. E. Allen et al disclose N-substituted oxopyrimidines in EP 0419048 A.

Similar structures are reported in EP 0424317 A by P. Herold et al.

The present invention differs from the above mentioned prior art in that it discloses non-peptidic amino substituted nitrogenous 6 membered heterocycles fused to 6–10 membered carbocyclic rings. The non-peptidic A II antagonists disclosed in the above mentioned prior art are either oxo-quinazolines, quinoline ethers, benzimidazoles, fused heterocyclic imidazoles or oxo-pyrimidines.

DESCRIPTION OF INVENTION

The present invention describes the composition and utility of novel compounds of the general formula I:

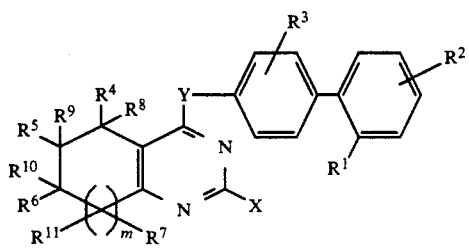

wherein

X is H, $NR^{12}R^{13}$, $OR^{14}$, CN, F, Cl, I, Br, perfluoroalkyl, alkyl, alkoxy, alkyl-OH, alkoxyalkyl, $-(CH_2)_nCO_2R^{14}$, $-(CH_2)_nCONR^{12}R^{13}$;

Y is $NR^{15}$, $NR^{18}CR^{16}R^{17}$, $CR^{16}R^{17}NR^{15}$;

$R^1$ is 5-tetrazolyl, $CO_2R^{14}$, $SO_3H$, $NHSO_2CH_3$, $NHSO_2CF_3$;

$R^2$, $R^3$ is H, alkyl, alkoxy, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$, $OR^{14}$, F, Cl, Br, I, $NR^{12}R^{13}$;

$R^4$–$R^{11}$ is H, F, alkyl, alkoxy, alkoxyalkyl, $-OCOR^{14}$, alkyl-OH, perfluoroalkyl, aralkyl, aryl, CN, $NO_2$, $SO_2R^{19}$, $-(CH_2)_nCO_2R^{14}$, $-(CH_2)_nCONR^{12}R^{13}$, OH, $OR^{14}$, $-NR^{12}R^{13}$, any two geminal groups can be O or $CH_2$;

$R^{12}$, $R^{13}$ is H, alkyl, aralkyl;

$R^{14}$ is H, alkyl, aralkyl, alkoxyalkyl;

$R^{15}$ is H, alkyl, $-(CH_2)_nCO_2R^{14}$, alkoxyalkyl, aralkyl, $-(CH_2)_nCONR^{12}R^{13}$, $OR^{14}$, perfluoroalkyl, alkyl-OH, $-COR^{14}$, $-CONR^{12}R^{13}$;

$R^{16}$, $R^{17}$ is H, alkyl, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$;

$R^{18}$ is H, alkoxyalkyl, alkyl-OH, perfluoroalkyl, aralkyl, $OR^{14}$, $-(CH_2)_nCO_2R^{14}$, $-(CH_2)_nCONR^{12}R^{13}$, alkyl, $-COR^{14}$, $-CONR^{12}R^{13}$;

$R^{19}$ is alkyl, aralkyl;

n is 0, 1, 2 or 3;

m is 1–5;

alkyl is defined as 1–8 carbons, branched or straight chain; perfluoroalkyl is defined as 1–6 carbons; aralkyl is defined as 7–12 carbons or 7–12 carbons substituted with fluorine, bromine or chlorine; aryl is defined as 6–10 carbons or 6–10 carbons substituted with fluorine, bromine or chlorine and the pharmaceutically acceptable salts, solvates and hydrates thereof.

The more preferred compounds of formula I are those wherein:

X is H, CN, F, Cl, I, Br, perfluoroalkyl, alkyl, alkoxy, alkyl—OH, alkoxyalkyl, $-(CH_2)_nCO_2R^{14}$, $-(CH_2)_nCONR^{12}R^{13}$;

Y is $NR^{15}$, $-NR^{18}CR^{16}R^{17}$, $-CR^{16}R^{17}$, $NR^{15}$;

$R^1$ is 5-tetrazolyl, $-CO_2H$, $SO_3H$, $NHSO_2CF_3$;

$R^2$, $R^3$ is H, alkyl, alkoxy, alkoxyalkyl, alkyl—OH, perfluoroalkyl, aralkyl, CN, $NO_2$, $SO_2R^{19}$, $-(CH_2)_nCO_2R^{14}$, $-(CH_2)_nCONR^{12}R^{13}$, $OR^{14}$, F, Cl, Br, I, $NR^{12}R^{13}$;

$R^4$–$R^{11}$ is H, F, alkyl, alkoxy, alkoxyalkyl, $OCOR^{14}$, alkyl—OH, perfluoroalkyl, aralkyl, aryl, CN, $NO_2$, $SO_2R^{19}$, $-(CH_2)_nCO_2R^{14}$, $-(CH_2)_nCONR^{12}R^{13}$, OH, $OR^{14}$, $NR^{12}R^{13}$, any two geminal groups can be O or $CH_2$;

$R^{12}$, $R^{13}$ is H, alkyl, aralkyl;

$R^{14}$ is H, alkyl, aralkyl, alkoxyalkyl;

$R^{15}$ is H, alkyl, $-(CH_2)_nCO_2R^{14}$, alkoxyalkyl, aralkyl, $-(CH_2)_nCONR^{12}R^{13}$, $OR^{14}$, perfluoroalkyl, alkyl—OH, $-COR^{14}$, $-CONR^{12}R^{13}$;

$R^{16}$, $R^{17}$ is H, alkyl, alkoxyalkyl, alkyl—OH, perfluoroalkyl, aralkyl, CN, $NO_2$, $SO_2R^{19}$, $-(CH_2)_nCO_2R^{14}$, $-(CH_2)_nCONR^{12}R^{13}$;

$R^{18}$ is H, alkoxyalkyl, alkyl—OH, perfluoroalkyl, aralkyl, $OR^{14}$, $-(CH_2)_nCO_2R^{14}$, $-(CH_2)_nCONR^{12}R^{13}$, alkyl, $-COR^{14}$, $-CONR^{12}R^{13}$;

$R^{19}$ is alkyl, aralkyl;

n is 0, 1, 2 or 3;

m is 1, 2, 3;

alkyl is defined as 1-8 carbons, branched or straight chain; perfluoroalkyl is defined as 1-6 carbons; aralkyl is defined as 7-12 carbons or 7-12 carbons substituted with fluorine, bromine or chlorine; aryl is defined as 6-10 carbons or 6-10 carbons substituted with fluorine, bromine or chlorine and the pharmaceutically acceptable salts, solvates and hydrates thereof.

Still further preferred compounds of formula I are those wherein:

X is perfluoroalkyl, alkyl, alkoxy, alkyl—OH;
Y is —$NR^{18}CR^{16}R^{17}$, —$CR^{16}R^{17}NR^{15}$;
$R^1$ is 5-tetrazolyl, —$CO_2H$, $SO_3H$, $NHSO_2CF_3$;
$R^2$, $R^3$ is H, alkyl, alkoxy, alkoxyalkyl, alkyl—OH, perfluoroalkyl, —CN, $NO_2$, —$(CH_2)_nCO_2R^{14}$, —$(CH_2)_nCONR^{12}R^{13}$, $OR^{14}$, F, Cl, Br, $NR^{12}R^{13}$;
$R^4$—$R^{11}$ is H, F, alkyl, alkoxy, alkoxyalkyl, $OCOR^{14}$, alkyl—OH, perfluoroalkyl, aralkyl, CN, —$(CH_2)_nCO_2R^{14}$, —$(CH_2)_nCONR^{12}R^{13}$, OH, $OR^{14}$, $NR^{12}R^{13}$, any two geminal groups can be O or $CH_2$;
$R^{12}$, $R^{13}$ is H, alkyl, aralkyl;
$R^{14}$ is H, alkyl, aralkyl, alkoxyalkyl;
$R^{15}$ is H, alkyl, —$(CH_2)_nCO_2$alkyl, —$(CH_2)_nCO_2H$, —COalkyl, —COH;
$R^{16}$, $R^{17}$ is H, —$CO_2H$, —$CO_2$alkyl;
$R^{18}$ is H, alkyl, —$(CH_2)_nCO_2$alkyl, —$(CH_2)_nCO_2H$, —COalkyl, —COH;
n is 0, 1, 2;
m is 1, 2, 3;
alkyl is defined as 1-8 carbons, branched or straight chain; perfluoroalkyl is defined as 1-6 carbons; aralkyl is defined as 7-12 carbons or 7-12 carbons substituted with fluorine, bromine or chlorine and the pharmaceutically acceptable salts, solvates and hydrates thereof.

The most preferred compounds of formula I are those wherein:

X is —$CF_3$, —$CH_3$, —iPr;
Y is —$NR^{18}CR^{16}R^{17}$;
$R^1$ is 5-tetrazolyl, —$CO_2H$;
$R^2$, $R^3$ is H, F;
$R^4$-$R^{11}$ is F, alkyl, —$OCOR^{14}$, perfluoroalkyl, —OH, —Oalkyl, any two geminal groups can be O;
$R^{14}$ is alkyl;
$R^{16}$, $R^{17}$ is H, —$CO_2H$, —$CO2CH_3$;
$R^{18}$ is H, alkyl, —$CH_2CO_2CH_3$, —$CO_2H$;
n is 0, 1;
m is 1, 2, 3;
alkyl is defined as 1-8 carbons, branched or straight chain; perfluoroalkyl is defined as 1-6 carbons and the pharmaceutically acceptable salts, solvates and hydrates thereof.

The following are specific examples given to illustrate the invention and should not be construed as limiting the invention set forth in the appended claims.

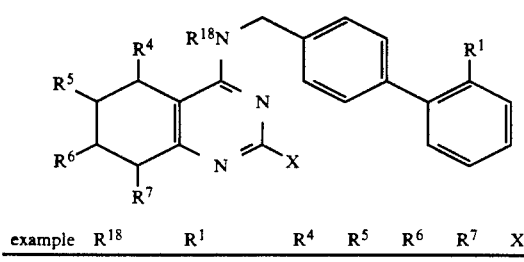

| example | $R^{18}$ | $R^1$ | $R^4$ | $R^5$ | $R^6$ | $R^7$ | X |
|---|---|---|---|---|---|---|---|
| 1 | H | $CO_2Na$ | H | H | H | H | $CF_3$ |
| 2 | H | 5-tetrazolyl | H | H | H | H | $CF_3$ |
| 3 | H | 5-tetrazolyl | H | H | H | H | $CH_3$ |
| 22 | H | 5-tetrazolyl | H | H | $CH_3$ | H | $CF_3$ |
| 23 | H | $CO_2Na$ | H | H | H | H | $CH_3$ |
| 12 | $CH_3$ | 5-tetrazolyl | H | H | H | H | $CF_3$ |
| 13 | H | 5-tetrazolyl | OAc | H | H | H | $CF_3$ |
| 14 | H | 5-tetrazolyl | H | H | H | H | iPr |
| 15 | H | 5-tetrazolyl | H | H | H | $CH_3$ | $CF_3$ |
| 16 | H | 5-tetrazolyl | OH | H | H | H | $CF_3$ |
| 10 | —$CH_2$—$CO_2Me$ | 5-tetrazolyl | H | H | H | H | $CF_3$ |
| 11 | —$CH_2$—$CO_2H$ | 5-tetrazolyl | H | H | H | H | $CF_3$ |
| 17 | H | 5-tetrazolyl | OMe | H | H | H | $CF_3$ |

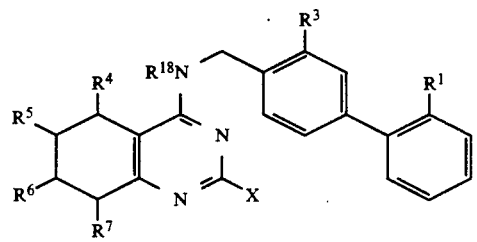

| example | $R^{18}$ | $R^1$ | $R^3$ | $R^4$ | $R^5$ | $R^6$ | $R^7$ | X |
|---|---|---|---|---|---|---|---|---|
| 18 | H | $CO_2Na$ | F | H | H | H | H | $CH_3$ |
| 19 | H | 5-tetrazolyl | F | H | H | H | H | $CF_3$ |
| 20 | H | 5-tetrazolyl | F | H | H | H | H | $CH_3$ |

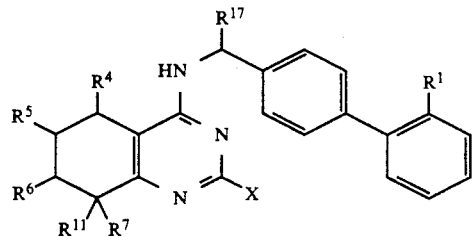

| example | $R^{17}$ | $R^1$ | $R^4$ | $R^5$ | $R^6$ | $R^7$ | $R^{11}$ | X |
|---|---|---|---|---|---|---|---|---|
| 24 | —$CO_2Me$ | 5-tetrazolyl | H | H | H | H | H | $CF_3$ |
| 25 | —$CO_2H$ | 5-tetrazolyl | H | H | H | H | H | $CF_3$ |
| 4 | H | 5-tetrazolyl | H | H | H | F | F | $CF_3$ |

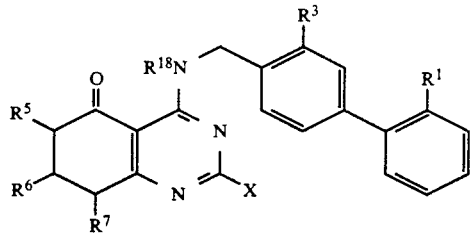

| example | $R^{18}$ | $R^1$ | $R^3$ | $R^5$ | $R^6$ | $R^7$ | X |
|---|---|---|---|---|---|---|---|
| 21 | H | 5-tetrazolyl | H | H | H | H | $CF_3$ |

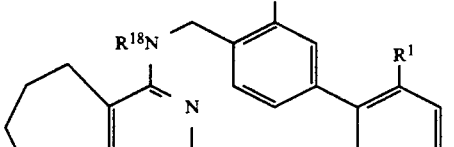

| example | $R^{18}$ | $R^1$ | $R^3$ | X |
|---|---|---|---|---|
| 6 | H | $CO_2Na$ | H | $CF_3$ |
| 5 | H | 5-tetrazolyl | H | $CF_3$ |
| 9 | H | 5-tetrazolyl | H | $CH_3$ |

-continued

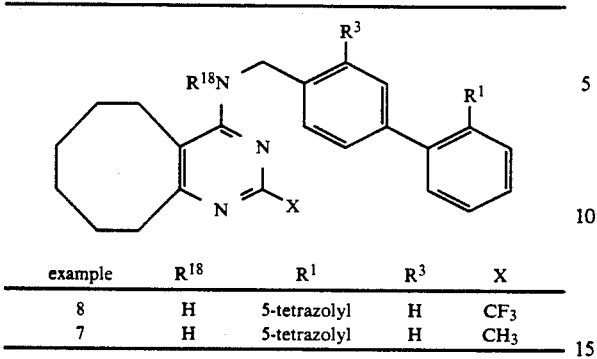

| example | R[18] | R[1] | R[3] | X |
|---------|-----|-----|-----|-----|
| 8 | H | 5-tetrazolyl | H | $CF_3$ |
| 7 | H | 5-tetrazolyl | H | $CH_3$ |

PROCESS OF INVENTION

The compounds of general formula 1 can be prepared as described in scheme 1. The 4-chloroquinazoline 2 can be reacted with the aminomethylbiphenyl 3 in the presence of a base such as sodium acetate, potassium carbonate or an organic base such as triethylamine in tetrahydrofuran, dioxane, dimethylformamide, dimethylsulfoxide or an alcohol at room temperature to reflux.

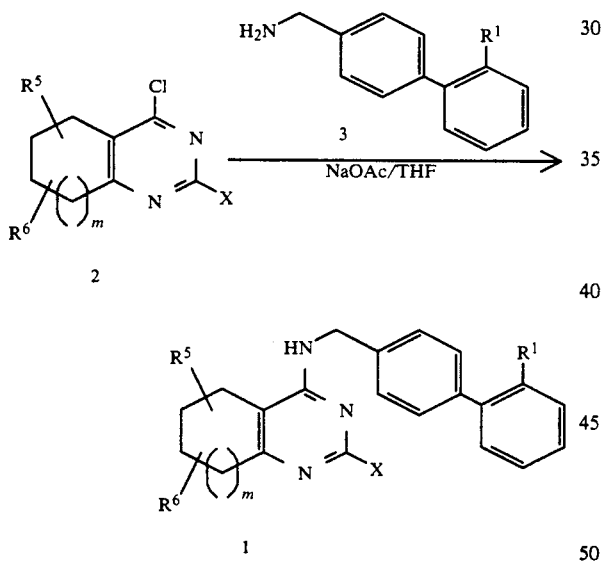

wherein $R^1$, $R^5$, m, $R^6$ and X are as defined above

Alternately compounds 1 can be prepared as shown in scheme 2. The bromophenylquinazolines 4 can be prepared by reacting the 4-chloroquinazoline 2 with p-bromobenzylamine, followed by protection of the benzylic nitrogen with a suitable protecting group as described by T. W. Greene, *Protective Groups in Organic Synthesis*, John Wiley & Sons, 1981. Conversion of 4 to its Grignard reagent, followed by the reaction of this with the oxazoline shown using the procedure of A. I. Meyers, et. al.; *J. Am. Chem. Soc.*, 97, 7383, 1975, yields 5. Conversion of the oxazoline 5 to its corresponding acid, ester and tetrazole can be carried out using the procedures described by Carini et. al. U.S. Pat. No. 4,880,804. for the preparation of 3.

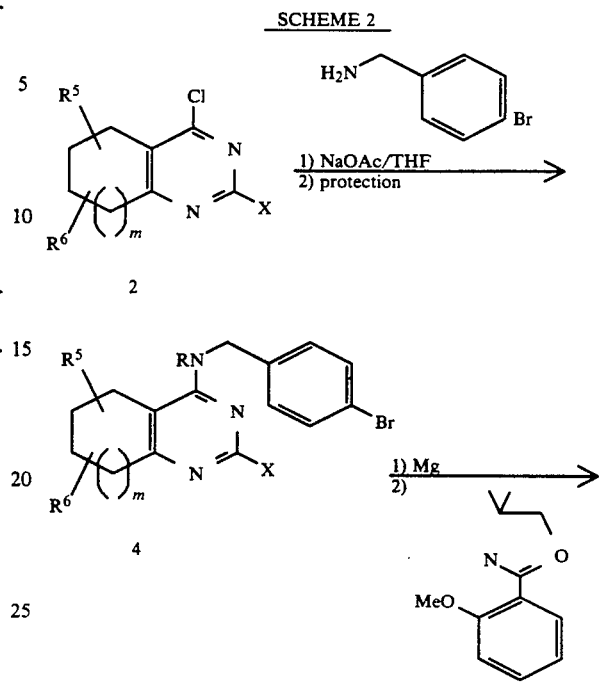

wherein $R^5$, $R^6$, m and X are as defined above and R is a protecting group

The preparation of compounds 3 shown in scheme 1 has been disclosed by Carini et. al. U.S. Pat. No. 4,880,804, EP 0324377, EP 0323841, EP 0253310. The preparation of substituted aminobiphenyl compounds such as 3b

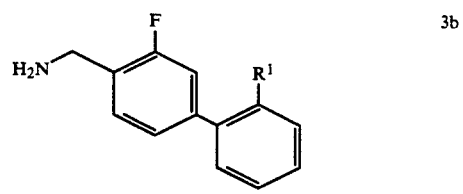

$R^1$ = 5-tetrazolyl, $-CO_2Me$, $-CO_2H$ can be carried out using similar chemistry.

Preparation of the 4-chlorotetrahydroquinazolines 2 can be carried out as shown in scheme 3. The suitably functionalized keto-ester 6 can be reacted with an amidine in the presence of an alkoxide base in a protic solvent to give the 4-tetrahydroquinazolone 7

SCHEME 3

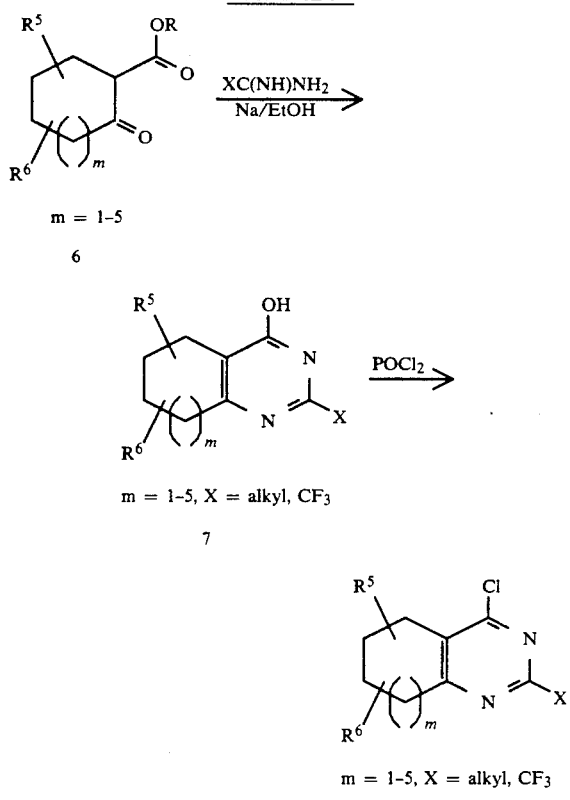

m = 1-5

6 m = 1-5, X = alkyl, CF₃

7 m = 1-5, X = alkyl, CF₃

2

(shown in its enol form in scheme 3). This quinazolone 7 is then reacted with phosphorousoxychloride in the presence of catalytic dimethylaniline to generate the required 4-chloro intermediate 2.

The preparation of compound 6 where $R^5$ and $R^6$ are geminal fluorine substitution is described in scheme 4. The dicarboxylic acid 8 is prepared using the procedure described in EP 0157567. This acid is converted to its diester, which is then reacted with DAST to yield the difluoro-diester 9. Cyclization of 9 to 6a is carried out using a base such as potassium t-butoxide in a suitable solvent.

SCHEME 4

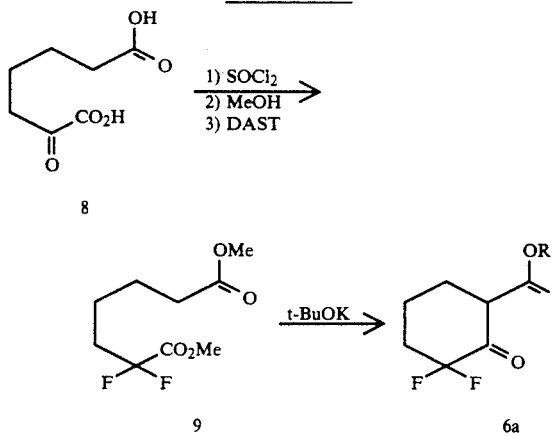

Alternately, compounds of general formula 1 can be prepared as described in scheme 5. The acetate func- tional group in 1b can be converted into other functional groups by conventional means.

SCHEME 5

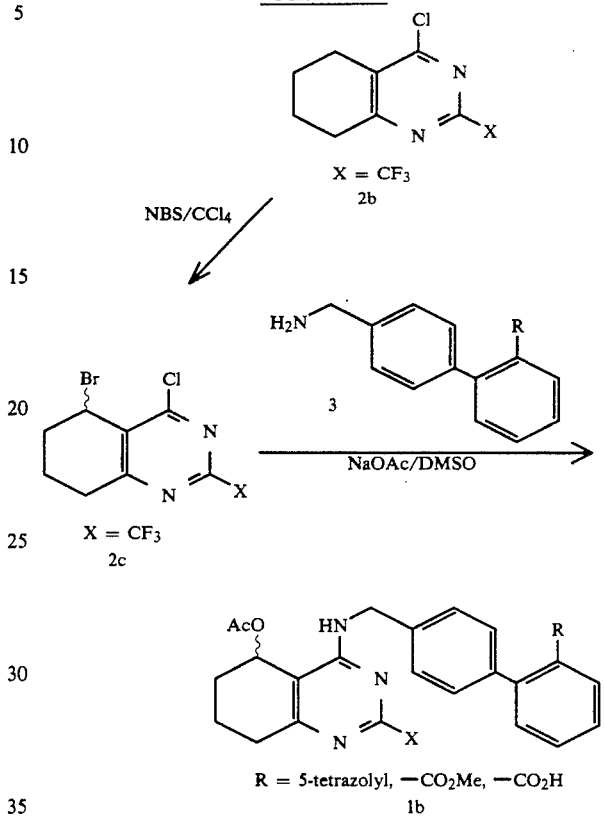

X = CF₃
2b

X = CF₃
2c

R = 5-tetrazolyl, —CO₂Me, —CO₂H
1b

The compounds of this invention may also form salts with inorganic or organic bases. Any pharmaceutically acceptible salts, hydrates and solvates of these compounds are within the scope of this invention. These salts may be, but are not limited to, ammonium salts, alkali metal salts such as sodium and potassium, alkaline earth metal salts such as calcium, dicyclohexylamine salts, TRIS salts, and salts of amino acids. These compounds may also be converted to N-oxides by treatment with hydrogen peroxide by conventional means.

The present invention also provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 1 to 50 mg. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compounds may also be administered in a parenteral dosing form.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics, $\beta$-blocking agents or ACE inhibitors.

The present invention further provides a compound of the invention for use as an active therapeutic substance. Compounds described in this invention are of particular use in the treatment of hypertension. They can also be used for the treatment of congestive heart-failure. In addition, the compounds of this invention also have therapeutic utility in the treatment of hyperlipidemia, and/or hypercholesterolemia.

The present invention further provides a method of treating hypertension in mammals including man, which comprises administering to the afflicted mammal an antihypertensive effective amount of a compound or a pharmaceutical composition of the invention.

The high affinity of the compounds for the angiotensin II receptor was established using a rat adrenal receptor binding assay, measuring the displacement of radiolabeled angiotensin II from the receptor, described as follows: Anesthetize male Sprague-Dawley rats (300–400 g body weight) with $CO_2$ and sacrifice by cervical dislocation. Dissect adrenal glands and keep in ice-cold sucrose buffer (0.2M sucrose, 1 mM EDTA, 10 mM Trizma base, pH=7.2). Remove medulla by squashing. Mince the cortex, rinse and homogenize in a chilled ground glass tissue grinder with 15 mL sucrose buffer. Centrifuge at $3000 \times g$ for 10 min. (Sorvall RCSC centrifuge, SS34 rotor 6200 rpm). Decant supernatant through gauze. Centrifuge combined supernatants at $12000 \times g$ for 13 min. (Beckman ultracentrifuge, 80Ti rotor, 13000 rpm). Centrifuge the supernatant from the previous step at $102000 \times g$ for 60 min. (Beckman ultracentrifuge, 80Ti rotor, 38200 rpm). All steps are carried out at 4° C. Resuspend the pellet in 0.5 mL assay buffer (50 mM Tris HCI, 5 mM $MgCl_2$, 0.2% BSA (protease-free), pH=7.4, 25° C.). Store on ice. Determine membrane protein by Lowry or Bradford assay with BSA as standard. The binding assay is performed in triplicate, in $12 \times 75$ mm plastic test tubes or in 96-well plate (final volume of 0.25 mL). Add 140 $\mu$L assay buffer. Add 10 $\mu$L cold A II (to give final concentrations of $10^{-10}$–$10^{-7}$M for standard curve and $10^{-4}$M for nonspecific binding), compounds (e.g., for final concentrations of 25 and 100 $\mu$M or 1 $\mu$M, 10 nM and 100 nM) in 50% DMSO, or 50% DMSO as a control. Add 50 $\mu$L membrane suspension (e.g., 10 $\mu$g protein). Preincubate for 30 min at 25° C. Add 50 $\mu$l $^{125}$I-A II which has been prepared as shown below (final concentration=1 nM). Incubate for 35 min at 25° C. Stop the incubation by adding 1 mL ice-cold buffer (assay buffer without BSA). Filter with GF/C filters on cell harvester (filters are presoaked in the assay buffer containing 1% polyethyleneimine). Rinse assay tubes 3X with 5 mL cold buffer (assay buffer without BSA). Cut and deposit the filter discs into test tubes and count on gamma counter for 1 min. Adjust the specific activity of $^{125}$I-A II purchased from New England Nuclear to 500 $\mu$Ci/nmole by adding cold A II in water. Calculate the quantities of hot A II and the cold A II needed and make the dilution. Aliquot, seal tight, and store frozen until needed. Calculate the concentration of the total A II (hot + cold) after dilution. On the day of assay, thaw the frozen aliquot and adjust the volume to give a concentration of 5 pmole/mL (or 0.25 pmole/50 $\mu$L) with assay buffer (+protease-free BSA). For final concentration of 1 nM $^{125}$I-A II in the assay, add 50 $\mu$L (or 0.25 pmole) per test tube to a final volume of 250 $\mu$L. The results of these binding assays are reported as the inhibitory concentration of the test compound necessary to achieve fifty percent displacement of radiolabeled angiotensin II from its receptor ($IC_{50}$), or the percent displacement of binding of A II at its receptor at $10^{-8}$M concentration of test compound (% I). The compounds of this invention displayed significant inhibition of A II binding in this assay. Typically these compounds displayed an $IC_{50}$ in this assay of less than or equal to 50 $\mu$M.

In accordance with their ability to antagonize angiotensin II, the compounds of this invention show antihypertensive action in the following A II-infused rat model. Rats are anesthetized with Dial-Urethane (0.60 mL/kg, ip) and the trachea cannulated with PE 240. Either one femoral artery and both femoral veins or the carotid artery and the corresponding jugular vein are cannulated with PE 50. If the jugular vein is cannulated, two cannulas are placed in the one vein. The initial portion of the duodenum (just distal to the stomach) is cannulated with PE 50 via a small midline incision. Arterial pressure and heart rate are measured from the arterial cannula. Ten to 15 min are allowed following surgery for stabilization of arterial pressure. Ganglion blockade is then produced by intravenous administration of mecamylamine at 3 mg/kg (1 mL/kg of a 3 mg/mL solution). Ganglion blockade causes a fall in arterial pressure of about 50 mmHg. Mecamylamine is given every 90 min throughout the remainder of the experiment. An A II infusion is then begun into the other venous cannula at 0.25 $\mu$g/kg/min (at 9.6 $\mu$L/min). The A II infusion returns arterial pressure to or slightly above the control level. Once arterial pressure has stabilized with the A II infusion, baseline values for means arterial pressure (MAP) and heart rate are taken. The test compound, suspended in methyl cellulose, is then administered via the duodenal cannula at 0.1, 3 or, 30 mg/kg in a volume of 1 mL/kg. Mean arterial pressure and heart rate values are tabulated at 15, 30, 60, 90, 120, 150, 180, 210, and 240 min after administration of the test compound. For example, the compound of Example 5 administered at 3 mg/kg id lowered the A II dependent blood pressure by an average of 45% one half hour postadministration.

As illustrated above the compounds of this invention are effective A II antagonists and therefore are useful for treating hypertension. They are also of value in the management of acute and chronic congestive heart failure, primary and secondary pulmonary hyperaldosteronism, secondary hyperaldosteronism, primary and secondary pulmonary hypertension, hypertension associated with oral contraceptive use, vascular disorders such as migraine, Raynaud's disease, luminal hyperplasia and the atherosclerotic process, renal diseases or renal complications of Part A To a flask under nitrogen was added 36 mL (76 mmol) of a 21% by weight solution of sodium ethoxide in ethanol, followed by the addition of 30 mL of absolute ethanol. To this mixture was added 7.3 g (65 mmol)

of trifluoroacetamidine, and 10 mL (64 mmol) of methyl 2-oxo-1-cycloheptanecarboxylate. The reaction mixture was refluxed overnight, cooled, and concentrated in vacuo. Water (100 mL) was added and the solution was acidified with 1N HCl until a precipitate appeared. The precipitate was collected and the filtrate was reacidified yielding additional white solid product. The two solids were combined and dried to yield 8.64 g (37.2 mmol, 58%) of the product. $^1$H-NMR (300 MHz, DMSO-d$_6$) $\delta$ 1.60–1.77 (m, 4H), 1.82–1.95 (m, 2H), 2.80–2.87 (m, 2H), 2.90–2.98 (m, 2H).

Part B

To a solution of the hydroxypyrimidine from part A (3.75 g, 16.1 mmol) in toluene (50 mL) was added 10 mL (107 mmol) of POCl$_3$ and 16 drops of dimethylaniline. The reaction mixture was refluxed for 3.5 h, cooled, and poured into a cold solution of a 1:1 mixture of water and diethyl ether. The organic layer was separated and washed with cold water and cold brine, dried (MgSO4), and concentrated to yield 3.7 g (14.76 mmol, 92%) of the chloropyrimidine as an off-white solid. The product was a single spot on TLC and was used directly for the next reaction.

Part C

To a solution of chloropyrimidine from part B (1.78 g, 7.1 mmol) in-BuOH (9 mL) was added 1.89 g (6.57 mmol) of N-[[2'-(1H-tetrazol-5-yl)[1,1'-biphenyl]-4-yl]methyl]amine hydrochloride and 3.2 g (39 mmol) of sodium acetate. The reaction mixture was refluxed for a total of 5 days, cooled, and poured directly on a flash chromatography column (20:80:2 MeOH:CHCl$_3$:NH$_4$OH) to yield 0.754 g (1.62 mmol, 25%) of product. $^1$H-NMR (300 MHz, DMSO-d$_6$) $\delta$ 1.53 (br, 4H), 1.79 (br, 2H), 2.65 (b, 2H), 2.79 (b, 2H), 4.53 (d, 2H, J=6 Hz), 7.02 (d, 2H, J=8 Hz), 7.15 (d, 2H, J=8 Hz), 7.27–7.45 (m, 4H), 7.52 (d, 1H, J=5 Hz), 7.96 (t, 1H, J=6 Hz). other diseases or therapies such as proteinuria, glomerulonephritis, glomerular sclerosis, scleroderma, diabetic nephropathy, end stage renal disease, renal transplant therapy and others. These compounds will also be useful in the treatment of left ventricular dysfunction, diabetic retinopathy, Alzheimers disease, in the enhancement of cognition, in treatment of elevated intraoccular pressure, and in the enhancement of retinal blood flow. These compounds will also be useful as antidepressants and anxiolytics and in the prevention or treatment of re-stenosis following angioplasty. The application of the compounds of this invention for these and similar disorders will be apparent to those skilled in the art.

The usefulness of these compounds as lipid lowering agents was assessed using cholesterol absorption in a cholesterol/cholic acid-fed rat model which is described as follows. Newly arrived rats are housed for 5 days in a room with reversed light/dark cycle and fed pelleted rat chow (Purina 5001). The food is removed, and the rats are placed on a daily 4 h/day feeding schedule (beginning at 9:00 AM) with normal chow for 7 days. After acclimation (total of 12 days) and randomization based on weight, dosing with drugs and feeding of cholesterol/cholic acid is initiated. Drug solubilized in vehicle (0.1 mL; olive oil, corn oil, 2% Tween 80, or carboxymethyl cellulose) is administered orally through a dosing needle immediately prior to (9:00 AM) and immediately following the 4 h feeding period. Dosing with drugs and feeding of the cholesterol/cholic acid diet is repeated for 4 days. On the morning of the 5th day, rats are sacrificed (decapitation), blood is collected and the livers are removed, weighed and stored frozen ($-80°$ C.). The animals are analyzed for total plasma cholesterol (TPC), high density lipoprotein cholesterol (HDLC, Sigma kit) and triglycerides (TG) on an Abbott Autoanalyzer. VLDL+LDL cholesterol is calculated by the difference between total and HDL cholesterol. HDL cholesterol/total cholesterol is also calculated. Typically the compounds of this invention show a 50% drop in total cholesterol at doses in the range of 100–200 mg/kg.

As illustrated above the compounds of this invention are effective lipid lowering agents and therefore are useful for treating hyperlipidemia and/or hypercholesterolemia.

Specific procedures are described in the following experimental examples. These examples are given to illustrate the invention and should not be construed as limiting the invention set forth in the appended claims.

EXPERIMENTAL

EXAMPLE 1

The synthesis of
4''-[[[5,6,7,8-tetrahydro-2-(trifluoromethyl)-4-quinazolinyl]amino]methyl][1,1'-biphenyl]-2-carboxylic acid Part A The preparation of
5,6,7,8-tetrahydro-2-trifluoromethyl-4-quinazolone To 10 mL of absolute ethanol under a nitrogen atmosphere was added 0.15 g of sodium metal. After all the sodium had reacted, 1.00 g of 2-carboethoxycyclohexanone was added followed by 0.78 g of 85% trifluoroacetamidine. The reaction was refluxed gently overnight. The reaction was cooled to room temperature and all solvents were removed by evaporation. The pH of the residue was adjusted to 6 with dilute hydrochloric acid and refluxed briefly and allowed to cool. The resulting solid was collected. (0.73 g, 57%): $^1$H NMR (DMSO-d$_6$, 300 MHz) $\delta$ 13.0 (s, 1H), 2.78 (m, 2H), 2.45 (m, 2H), 1.78 (m, 4H).

Part B

The preparation of
4-chloro-5,6,7,8-tetrahydro-2-trifluoromethylquinazoline

To a mixture of 6.0 mL of phosphorus oxychloride and 1.0 mL of dimethylaniline in 20 mL of toluene was added 3.0 g of 5,6,7,8-tetrahydro-2-trifluoromethyl-4-quinazolone. The resulting mixture was refluxed for 3 hours and then cooled to room temperature. The reaction mixture was poured into a ice cold mixture of diethyl ether and water. The organic layer was recovered washed with brine, dried over anhydrous magnesium sulfate, filtered and evaporated to yield the product as a brown solid (3.46 g).

Part C

The synthesis of
4'-[[[5,6,7,8-tetrahydro-2-(trifluoromethyl)-4-quinazolinyl]amino]methyl][1,1'-biphenyl]-2-carboxylic acid To 10 mL of n-butanol were added 0.526 g of 4-chloro-5,6,7,8-tetrahydro-2-trifluoromethylquinazoline, 0.408 g of 4' aminomethyl-(1,1'-biphenyl)-2-carboxylic acid and 1.1 g of sodium acetate. The resulting mixture was refluxed for 3 days, cooled to room temperature and all solvents were removed by evaporation. The residue was taken up in ethyl acetate and washed with brine. The organic layer was dried over anhydrous magnesium sulfate, filtered and evaporated to yield an off-white solid which was purified by silica chromatography to yield the desired product (0.39 g, 59%). The compound was characterized as its sodium salt: $^1$H NMR (DMSO-d$_6$, 400 MHz) δ 7.88 (t, J=6.0 Hz, 1H), 7.39 (m, 2H), 7.28 (m, 3H), 7.17 (m, 3H), 4.60 (d, J=5.9 Hz, 2H), 2.61 (m, 2H), 2.38 (m, 2H), 1.74 (m, 4H); negative FAB-MS m/e 448(M-H), 426(M-Na). Anal. calcd for C$_{23}$H$_{19}$F$_3$N$_3$NaO$_2$·1.0H$_2$O: C, 59.10; H, 4.53; N, 8.99. Found: C, 59.03; H, 4.48; N, 9.09.

EXAMPLE 2

The preparation of
5,6,7,8-tetrahydro-N-[[2'-(1H-tetrazol-5-yl)[1,1'-biphenyl]-4-yl]methyl]-2-(trifluoromethyl)-4-quinazolinamine To 10 mL of a 5:1 mixture of n-butanol/methanol were added 1.42 g of 4-chloro-5,6,7,8-tetrahydro-2-trifluoromethylquinazoline, 1.73 g of N-[[2'-(1H-tetrazol-5-yl)[1,1'-biphenyl]-4-yl]methyl]amine hydrochloride and 2.7 g of sodium acetate. The resulting mixture was heated at reflux for 5 days and then cooled to room temperature. All solvents were removed by evaporation and the resulting residue was purified on silica to yield 1.35 g (50%) of the desired product. The compound was characterized as its potassium salt: $^1$H NMR (DMSO-d$_6$, 400 MHz) δ 7.78 (t, J=6.0 Hz, 1H), 7.50 (m, 1H), 7.32 (m, 3H), 7.15 (m, 2H), 7.03 (m, 2H), 4.57 (d, J=6.0 Hz, 2H), 2.61 (m, 2H), 2.38 (m, 2H, 1.75 (m, 4H); negative FAB-MS m/e 488(M-H), 450(M-K). Anal. calcd for C$_{23}$H$_{19}$F$_3$KN$_7$·0.5H$_2$O: C, 55.41; H, 4.04; N, 19.67. Found: C, 55.66; H, 4.09; N, 19.46.

EXAMPLE 3

The preparation of
5,6,7,8-tetrahydro-N-[[2'-(1H-tetrazol-5-yl)[1,1'-biphenyl]-4-yl]methyl]-2-methyl-4-quinazolinamine

Part A

The preparation of
5,6,7,8-tetrahydro-2-methyl-4-quinazolone

To 50 mL of absolute ethanol under a nitrogen atmosphere was added 5.65 g of sodium metal. After all the sodium had reacted, 20.15 g of 2-carboethoxycyclohexanone was added followed by 14.50 g of acetamidine hydrochloride. The reaction was refluxed gently overnight. The reaction was cooled to room temperature and all solvents were removed by evaporation. The pH of the residue was adjusted to 6 with dilute hydrochloric acid and refluxed briefly and allowed to cool. The resulting solid was collected. Successive crops of solid were collected by concentration of the mother liquors (13.1 g, 65%): $^1$H NMR (DMSO-d$_6$, 300 MHz) δ 12.18 (s, 1H), 2.22 (m, 2H), 2.15 (m, 2H), 2.10 (s, 3H), 1.65 (m, 4H).

Part B

The preparation of
4-chloro-5,6,7,8-tetrahydro-2-methylquinazoline

To a mixture of 4.5 mL of phosphorus oxychloride and 20 drops of dimethylaniline in 50 mL of toluene was added 4.2 g of 5,6,7,8-tetrahydro-2-methyl-4-quinazolone. The resulting mixture was refluxed for 3 hours and then cooled to room temperature. The reaction mixture was poured into a ice cold aqueous potassium carbonate. After stirring for 5 minutes the mixture was added to diethyl ether/water. The organic layer was recovered washed with brine, dried over anhydrous magnesium sulfate, filtered and evaporated to yield a yellow oil. This oil was purified on silica to yield the desired compound as a light yellow solid (4.45 g, 95%): $^1$H NMR (DMSO-d$_6$, 300 MHz) δ 2.78 (m, 2H), 2.64 (m, 2H), 2.50 (s, 3H), 1.78 (m, 4H).

Part C

The preparation of
5,6,7,8-tetrahydro-N-[[2'-(1H-tetrazol-5-yl)[1,1'-biphenyl]-4-yl]methyl]-2-methyl-4-quinazolinamine To 10 mL of dimethylformamide were added 0.57 g of 4-chloro-5,6,7,8-tetrahydro-2-methylquinazoline, 0.45 g of N-[[2'-(1H-tetrazol-5-yl)[1,1'-biphenyl]-4-yl]methyl]amine hydrochloride and 1.30 g of anhydrous potassium carbonate. The resulting mixture was heated at 95° C. for 5 days and then cooled to room temperature. The resulting mixture was run through a silica plug (methanol/chloroform/ammonia eluant) and after all solvent was removed by evaporation the resulting residue was purified on silica to yield 0.19 g (31%) of the desired product. The compound was characterized as its potassium salt: $^1$H NMR (DMSO-d$_6$, 400 MHz) δ 7.50 (m, 1H), 7.32 (m, 3H), 7.11 (d, J=8.2 HZ, 2H), 7.02 (m, 3H), 4.57 (d, J=6.0 Hz, 2H), 2.48 (m, 4H);, 2.24 (s, 3H), 1.71 (m, 4H); negative FAB-MS m/e 433(M-H); 396(M-K). Anal. calcd for C$_{23}$H$_{22}$KN$_7$·0.85H$_2$O: C, 61.53; H, 5.30; N, 21.84. Found: C, 61.74; H, 5.25; N, 21.47.

The following examples were or can be prepared using the procedures described for Examples 1-3.

| example | R$^{18}$ | R$^1$ | R$^3$ | R$^4$ | R$^5$ | R$^6$ | R$^7$ | X |
|---|---|---|---|---|---|---|---|---|
| 22 | H | 5-tetrazolyl | H | H | H | CH$_3$ | H | CF$_3$ |
| 23 | H | CO$_2$Na | H | H | H | H | H | CH$_3$ |
| 14 | H | 5-tetrazolyl | H | H | H | H | H | iPr |
| 15 | H | 5-tetrazolyl | H | H | H | H | CH$_3$ | CF$_3$ |
| 18 | H | CO$_2$Na | F | H | H | H | H | CH$_3$ |
| 19 | H | 5-tetrazolyl | F | H | H | H | H | CF$_3$ |
| 20 | H | 5-tetrazolyl | F | H | H | H | H | CH$_3$ |

EXAMPLE 4

The preparation of
8,8-Difluoro-5,6,7,8-tetrahydro-N-[[2'-(1H-tetrazol-5-yl)[1,1'-biphenyl]-4-yl]methyl]-2-(trifluoromethyl)-4-quinazolinamine sodium salt

Part A

A solution of 3.23 g (18.6 mmol) of 2-oxo-heptanedicarboxylic acid (as prepared in EPA 157 567) and thionyl chloride (6.78 mL, 92.8 mmol) in chloroform was refluxed for 1 hour. The reaction mixture was concentrated in vacuo, diluted with methylene chloride (20 mL) and treated with excess methanol. The reaction was stirred at room temperature for 16 hours and concentrated. Purification by flash chromatography (25% ethyl acetate/hexane) gave 737 mg of dimethyl 2-oxohepatanoate. $^1$H-NMR (DMSO; 400 MHz) d 3.76 (s, 3H), 3.57 (s, 3H), 2.82 (t, 2H), 2.30 (t, 2H), and 1.47-1.53 ppm (m, 4H); IR (film) 1730 cm$^{-1}$. Anal. Calcd. for $C_9H_{14}O_5$: C, 53.46; H, 6.98. Found: C, 53.44; H, 6.73.

Part B

To a solution of 330 μL (2.50 mmol) of diethylaminosulfur trifluoride (DAST) in 3 mL of methylene chloride was added dropwise a solution of the product from Part A (459 mg, 2.27 mmol) in 5 mL of methylene chloride. The reaction mixture was stirred at room temperature for 20 hours, quenched with water (30 mL) and extracted into ether. The combined organic extracts were dried (MgSO$_4$), concentrated, purified by flash chromatography (20% ethyl acetate/hexane) to give 286 mg (56% yield) of dimethyl 2,2-difluoroheptanoate: $^1$H-NMR (DMSO; 400 MHz) d 3.83 (s, 3H), 3.58 (s, 3H), 2.33 (t, 2H), 2.03-2.16 (m, 2H), 1.52-1.59 (m, 2H), and 1.34-1.42 ppm (m, 2H); IR (film) 1775 and 1740 cm$^{-1}$; EI mass spectrum, m/e 225 (M+H)$^+$. Anal. Calcd. for $C_9H_{14}F_2O_4.0.25H_2O$: C, 47.26; H, 6.39. Found: C, 47.46, H, 6.12.

Part C

To a refluxing mixture of potassium t-butoxide (1.31 g, 11.1 mmol) in benzene (10 mL) was added a solution of the product from Part B (2.49 g, 11.1 mmol) in benzene (30 mL). The reaction mixture was stirred at reflux overnight and then at room temperature for 2 days. The reaction mixture was quenched with 1N HCl (75 mL) and was extracted into ether. The combined organic extracts were dried (MgSO$_4$) and concentrated to give crude 2.11 g (99%) of 2,2-difluoro-6-carbomethoxycycloheanone (mixture of keto and enol forms by nmr), which was used without further purification: $^1$H-NMR (DMSO; 400 MHz; partial) d 11.4 (s; enol H), 3.78 (s, 3H); IR (film) 1770, 1740, and 1670 cm$^{-1}$; EI mass spectrum, m/e 192. Anal. Calcd. for $C_8H_{10}F_2O_3.0.5H_2O$: C, 47.76; H, 5.51. Found: C, 47.92; H, 5.34.

Part D

A mixture of the product from Part C (164 mg, 0.854 mmol) and trifluoroacetamidine (95.7 mg, 0.854 mmol) in methanol (5 mL) containing 391 μL (1.71 mmol) of 4.37M sodium methoxide in methanol was heated in a sealed tube a 90° C. for 16 hours. The reaction mixture was cooled to room temperature, adjusted to pH 7 with 1N HCl and then pH 7 buffer. The reaction mixture was extracted into ether, dried (MgSO$_4$), and concentrated to give 111 mg (51% yield) of crude product which was used without further purification: EI mass spectrum, m/e 254.

Part E

To a mixture of the product from Part D (95 mg, 0.374 mmol) and phosphorous oxychloride (312 μL, 3.37 mmol) in toluene was added N,N-dimethylaniline (30 μL, 0.236 mmol). The reaction mixture was reluxed for 3 days. The reaction mixture was cooled to room temperature, carefully poured into ice water (20 mL), and extracted into 20% THF/CH$_2$Cl$_2$. The organic extracts were dried (K$_2$CO$_3$) and concentrated to give 77 mg (75% yield) of crude product: $^1$H-NMR (DMSO; 300 MHz) d 2.91 (br t, 2H), 2.38-2.45) (m, 2H), and 1.98-2.02 ppm (m, 2H); EI mass spectrum, m/e 272.

Part F

A mixture of the product from Part E (61 mg, 0.223 mmol) and N-[[2'-(1Htetrazol-5-yl)[1,1'-biphenyl]-4-yl]methyl]amine hydrochloride (61.2 mg, 0.223 mmol) in DMF containing 154 mg (1.12 mmol) of K$_2$CO$_3$ was heated at 100° C. for 16 hours. The reaction mixture was cooled to room temperature, adjusted to pH 7 with 1.44M ethanolic HCl and filtered. The filtrate was concentrated and flash chromatographed (CH$_2$Cl$_2$/MeOH/NH$_4$OH 76.5:19:4.5)) to give 51 mg of product (47% yield): $^1$H-NMR (DMSO; 300 MHz) d 8.39 (br t, 1H), 7.41-7.60 (M, 4H), 7.24 (d, 2H), 7.05 (d, 2H), 4.64 (d, 2H), 4.58 (s, 1H), 2.54 (br 2H), 2.2-2.4 (m, 2H), and 1.2-1.95 ppm (m, 2H); positive FAB mass spectrum, m/e 488 (M+H).

Part G

To a solution of the product prepared using the procedure in Part F (373 mg, 0.766 mmol) in methanol (10 mL) was added dropwise a solution of 4.6M sodium methoxide (167 μL (0.766 mmol) in methanol. The solution was stirred at room temperature for 30 minutes and concentrated. The material was dissolved in hot THF, filtered, and triturated into cold petroleum ether (100 mL) to afford the title compound (220 mg) as an off-white solid, mp 215°-225° C.; $^1$H-NMR (DMSO; 400 MHz) d 8.36 (t, 1H), 7.53 (dd, 1H), 7.28-7.38 (m, 3H), 7.19 (d, 2H), 7.06 (d, 2H), 4.62 (d, 2H), 2.50-2.55 m, 2H), 2.29-2.33 (m, 2H), and 1.91-1.94 ppm (m, 2H); IR (KBr) 3430 and 1600 cm$^{-1}$; positive mass spectrum, m/e 510 (M+H), 532 (M+Na). Anal. Calcd. for $C_{23}H_{17}F_5N_7Na.1H_2O$: C, 52.37; H, 3.63; N, 18.59. Found: C, 52.71; H, 3.57; N, 18.59.

EXAMPLE 5

The preparation of 6,7,8,9-tetrahydro-N-[[2'-(1H-tetrazol-5-yl)[1,1'-biphenyl]-4-yl]methyl]-2-(trifluoromethyl)-5H-cycloheptapyrimidin-4-amine potassium salt hydrate.

Part D

To the product from part C (0.19 g, 0.4 mmol) in MeOH (2 mL) was added 0.4 mL of 1N KOH. The ice bath was removed and the reaction mixture was allowed to stand at RT for 10 minutes. The solution was concentrated to yield 0.164 g, (0.33 mmol, 83%) of the title compound as a yellow solid. $^1$H-NMR (400 MHz, DMSO-d$_6$) δ 1.46-1.60 (m, 4H), 1.76-1.84 (m, 2H), 2.66-2.74 (m, 2H), 2.78-2.84 (m, 2H), 4.53 (d, 2H, J=5.8 Hz), 7.04 (d, 2H, J=8.1 Hz), 7.13 (d, 2H, J=8.2 Hz), 7.26-7.36 (m, 3H), 7.49 (m, 1H, J=6.0 Hz), 7.96 (t, 1H, J=5.9 Hz); negative FAB-MS m/e 464 (M-K)$^-$. Anal Calcd for $C_{24}H_{21}N_7F_3K.H_2O$: C, 55.26; H, 4.44; N, 18.80. Found: C, 54.98; H, 4.42; N, 18.56.

EXAMPLE 6

The preparation of 4'-[[[6,7,8,9,-tetrahydro-2-(trifluoromethyl)-5H-cycloheptapyrimidin-4-yl]amino]methyl][1,1'-biphenyl]-2-carboxylic acid sodium salt hemihydrate

Part A

To the chloropyrimidine (0.305 g, 1.2 mmol) of example 1, part B in THF was added methyl 4'-aminomethyl- (1,1'-biphenyl)-2-carboxylate (0.65 g, 2.69 mmol), and NaOAc (0.677 g, 8.26 mmol). The reaction mixture was stirred at room temperature for 4 days. The reaction mixture was concentrated, partitioned between EtOAc and H$_2$O, the organic layer was washed with brine, dried (MgSO$_2$), and concentrated. Flash chromatography (0–3% MeOH/CHCl$_3$) was utilized to provide 0.26 g (0.57 mmol, 47%) of pure product as a white solid: $^1$H-NMR (300 MHz, CDCl$_3$) δ 1.50–1.78 (m, 4H), 1.85–1.95 (m, 2H), 2.56–2.60 (m, 2H), 2.95–3.01 (m, 2H), 3.68 (s, 3H), 4.78 (d, 2H, J=8 Hz), 7.25–7.60 (m, 8H), 7.83 (d, 1H, J=8 Hz); EI-MS m/e 455.

Part B

To the product from part A (0.126 g, .0.27 mmol) in MeOH (5 mL) was added 1N NaOH (0.84 mL). The reaction mixture was refluxed overnight, cooled, and a large excess of water was added. The aqueous layer was washed gently with diethyl ether, acidified with KHSO$_4$ to a pH of about 2, and extracted with EtOAc. The organic layer was washed with brine, dried (MgSO$_4$), and concentrated to yield 0.096 g (79%) of product as a white solid. $^1$H-NMR (300 MHz, DMSO-d$_6$) δ 1.50–1.60 (m, 4H), 1.76–1.84 (m, 2H), 2.68–2.74 (m, 2H), 2.80–2.84 (m, 2H), 4.60 (d, 2H, J=6 Hz), 7.20–7.58 (m, 7H), 7.68 (d, J=5 Hz), 8.01 (t, 1H, J=6 Hz).

Part C

To the product from part B (0.87 g, 0.199 mmol) in MeOH (1.3 mL) was added 0.2 mL 1N NaOH. The reaction mixture was allowed to stand at room temperature for about 1 hour and concentrated to yield 0.87 g (0.188 mmol, 94%) of the title compound as a light yelow solid: $^1$H-NMR (400 MHz, DMSO-d$_6$) δ 1.53–1.59 (m, 4H), 1.78–1.82 (m, 2H), 2.68–2.74 (m, 2H), 2.79–2.82 (m, 2H), 4.56 (d, 2H, J=5.7 Hz), 7.14–7.41 (m, 8H), 8.00 (t, 1H, J=5.8 Hz); negative FAB-MS m/z 440 (M-Na)$^-$, 462 (M-H)$^-$. Anal Calcd for C$_{24}$H$_{21}$N$_3$F$_3$O$_2$·Na·0.5 H$_2$O: C, 61.01; H, 4.69; N, 8.89. Found: C, 61.35; H, 5.00; N, 8.35.

Example 7

The preparation of 5,6,7,8,9,10-hexahydro-2-methyl-N-[[2'-(1H-tetrazol-5-yl)[1,1'-biphenyl]-4-yl]methyl]-4-cyclooctapyrimidinamine sodium salt Part A A solution of methyl 2-cyclooctanone carboxylate (2.52 g, 13.7 mmol) and acetamidine (1.53 g, 13.7 mmol) in methanol (13 mL) containing sodium methoxide (6.27 mL, 27.4 mmol of 4.37M sodium methoxide in methanol) was stirred at reflux for 16 h. The reaction mixture was cooled to room temperature, adjusted to pH 7 using 2N HCl and pH 7 buffer. The reaction mixture was extracted into 20% THF-CH$_2$Cl$_2$. The organic extracts were dried (MgSO$_4$) and concentrated to give 1.84 g (70% yield) of product: $^1$H-NMR (300 MHz, DMSO-d$_6$) δ 12.1 (bs, 1H), 2.5–2.6 (m, 4H), 2.21 (s, 3H), 1.6 (m, 2H), 1.51 (m, 2H), and 1.36 ppm (m, 4H); IR (KBr) 3430 and 1645 cm$^{-1}$. Anal. Calcd for C$_{11}$H$_{16}$N$_2$O: C, 68.71; H, 8.39; N, 14.57. Found: C, 68.64; H, 8.29; N, 14.15.

Part B

The product from part A (1.83 g, 9.53 mmol), POCl$_3$ (13.1 g, 86 mmol) and N,N-dimethylaniline (0.73 g, 6.0 mmol) in toluene (100 mL) were heated at reflux for 1 h. The reaction mixture was cooled to room temperature and slowly poured into crushed ice-water (250 mL). The reaction mixture was extracted into ether and 20% THF-CH$_2$Cl$_2$. The combined organic extracts were dried (K$_2$CO$_3$) and concentrated to give 1.89 g (94% yield) of product which was used without further purification: $^1$-NMR (400 MHz, DMSO-d$_6$) δ 2.85–2.90 (m, 4H), 2.52 (s, 3H), 1.6–1.7 (m, 4H), and 1.26–1.39 ppm (m, 4H); EI-MS m/e 210 and 212.

Part C

A mixture of the product from part B (213 mg, 1.0 mmol) and N-[[2'-(1H-tetrazol-5-yl)[1,1'-biphenyl]-4-yl]methyl]amine hydrochloride (277 mg, 1.0 mmol) and K$_2$CO$_3$ (697 mg, 5.1 mmol) in DMF (5 mL) was stirred in a sealed tube at 100° C. for 5 days. The reaction mixture was cooled to room temperature and carefully treated with 7 mL of 1.4M ethanolic HCl. The reaction mixture was filtered and concentrated in vacuo. Purification by flash chromatography (CH$_2$Cl$_2$-MeOH-NH$_4$OH (76.5:19:4.5) gave 127 mg (30% yield) of product: $^1$H-NMR (400 MHz, DMSO-d$_6$) δ 8.05 (br t, 1H), 7.4–7.6 (m, 4H), 7.16 (d, 2H), 7.04 (d, 2H), 4.64 (d, 2H), 2.69 (br, 4H), 2.33 (s, 3H), 1.57–1.66 (br d, 4H), and 1.31–1.41 ppm (br d, 4H); positive FAB MS m/e 426 (M+H)$^+$.

Part D

A slurry of 579 mg (1.36 mmol) of the product from part C in MeOH (20 mL) was treated with 295 μL (1.36 mmol) of 4.6M sodium methoxide in MeOH. After stirring for 30 minutes at ambient temperature, the reaction mixture was concentrated. The residue was dissolved in hot THF, filtered, and cooled to room temperature. Trituration with cold petroleum ether gave 382 mg of the title compound. mp 183°–200° C.: $^1$H-NMR (400 MHz, DMSO-d$_6$) δ 7.50 (dd, 1H), 7.27–7.41 (h, 3H), 7.24 (t, 2H), 7.08 d, 2H), 7.02 (d, 2H), 4.57 (d, 2H), 2.63–2.66 (m, 4H), 2.25 (s, 3H), 1.5–1.6 (m, 4H), 1.37 m, 2H), and 1.27 ppm (m, 2H); negative FAB MS m/e 446 (M-H), 424 (M-Na). Anal. Calcd for C$_{25}$H$_{26}$N$_7$Na·1.25 H$_2$O: C, 63.88; H, 6.08; N, 20.98. Found: C, 63.59; H, 5.86; N, 20.82.

EXAMPLE 8

The preparation of 5,6,7,8,9,10-hexahydro-N-[[2'(1H-tetrazol-5-yl)[1,1'-biphenyl]-4-yl]methyl]-2-(trifluoromethyl)-4-cyclooctapyrimidinamine sodium salt Part A By analogy with Part A of Example 5, the product was prepared in 51% yield from trifluoroacetamidine and methyl 2-cyclooctanone carboxylate by heating in a sealed tube at 90° C. Purification was achieved by flash chromatography using 5% MeOH—CH$_2$Cl$_2$ as eluant: $^1$H-NMR (200 MHz, DMSO-d$_6$) δ 12.5 (bs, 1H), 2.86 (t, 2H), 2.74 (t, 2H), 1.63–1.69 (m, 4H), and 1.35 ppm (br s, 4H); IR (KBr) 3430 and 1650 cm$^{-1}$; EI MS m/e 246. Anal. Calcd for C$_{11}$H$_{13}$F$_3$N$_2$O: C, 53.66; H, 5.32; N, 11.38. Found: C, 53.85; H, 5.33; N, 11.01.

Part B

By analogy with Part B of Example 5, the product was prepared in 95% yield from the product of part A: $^1$H-NMR (400 MHz, DMSO-d$_6$) δ 2.98–3.05 (m, 4H), 2.48–2.50 (m, 4H), and 1.28–1.42 ppm (m, 4H); EI MS m/e 264 and 266.

Part C

By analogy with Part C of Example 5, the product was prepared in 54% yield from the product of part B and N-[[2'-(1H-tetrazol-5-yl)[1,1'-biphenyl]-4-yl]methyl]-amine hydrochloride using a sealed tube at 100° C. for 16 h: $^1$H-NMR (400 MHz, DMSO-d$_6$) δ 7.94 (t, 1H), 7.42–7.59 (m, 4H), 7.19 (d, 2H), 7.03 (d, 2H), 4.59 (d, 2H), 2.70–2.77 (m, 4H), 1.57–1.68 (m, 4H), and 1.26–1.40 ppm (m, 4H); IR (KBr) 2910 and 1585 cm$^{-1}$; positive FAB 480 (M+H), 502 (M+Na). Anal. Calcd for C$_{25}$H$_{24}$F$_3$N$_7$.0.5 H$_2$O: C, 61.47; H, 5.16. Found: C, 61.18; H, 5.29.

Part D

Using the procedure of Part D in Example 5, 635 mg of the title compound was prepared from 791 mg of the product from part C: mp 177°–195° C.; $^1$H-NMR (400 MHz, DMSO-d$_6$) δ 7.93 (t, 1H), 7.50 (d, 1H), 7.26–7.36 (m, 3H), 7.11 (d, 2H), 7.04 (d, 2H), 5.47 (d, 2H), 2.73 (m, 4H), 1.62–1.65 m, 4H), and 1.28–1.39 ppm (m, 4H); IR (KBr) 3350 (br); negative FAB MS m/e 500 (M-H), 478 (M-Na). Anal. Calcd C$_{25}$H$_{23}$N$_7$F$_3$Na.0.5H$_2$O: C, 57.79; H, 4.85. Found: C, 57.86; H, 5.04.

EXAMPLE 9

The preparation of 6,7,8,9-tetrahydro-2-methyl-N-[[2'-(1H-tetrazol-5-yl)[1,1'-biphenyl]-4-yl]methyl]-5H-cycloheptapyrimidin-4-amine sodium salt

Part A

Using the procedure Part A of Example 5, the product was prepared from methyl 2-cycloheptanone carboxylate in 62% yield: $^1$H-NMR (400 MHz, DMSO-d$_6$) δ 2.61–2.65 (m, 2H), 2.54–2.58 (m, 2H), 2.19 (s, 3H), 1.72–1.78 (m, 2H), 1.40–1.55 (m, 2H), and 1.39–1.45 ppm (m, 2H); IR (KBr) 1650 cm$^{-1}$; EI MS m/e 178, 163 and 149.

Part B

Using the procedure of Part B of Example 5, the product was parpared from the product of part A. The crude material was used without purification; an analytical sample was obtained by flash chromatography (3% MeOH/CH$_2$Cl$_2$): $^1$H-NMR (400 MHz, DMSO-d$_6$) δ 2.90–2.96 (m, 4H), 2.50 (s, 3H), 1.79–1.84 (m, 2H), and 1.54–1.63 ppm (m, 4H); EI MS m/e 196, 198, 161. Anal. Calcd for C$_{10}$H$_{13}$ClN$_2$: C, 61.07; H, 6.66; N, 14.24. Found: C, 60.95; H, 6.62; N, 14.02.

Part C

The product was prepared in 43% yield from the coupling of the product from part B and N-[[2'-(1H-tetrazol-5-yl)[1,1'-biphenyl]-4-yl]methyl]amine hydrochloride at 100° C. for 7 days using the procedure of Part C of Example 3: $^1$H-NMR (300 MHz, DMSO-d$_6$) δ 7.90 (br t, 1H), 7.44–7.61 (m, 4H), 7.19 (d, 2H), 7.7.03 (d, 2H), 4.60 (d, 2H), 2.71–2.75 (m, 2H), 2.61–2.65 (m, 2H), 2.30 (s, 3H), 1.77–1.79 (m, 2H), and 1.48–1.57 ppm (m, 4H).

Part D

Using the procedure of part D of Example 5, 200 mg of the title compound was prepared from 468 mg of the product from part C: mp 180°–195° C.; $^1$H-NMR (400 MHz, DMSO-d$_6$) δ 7.48 (dd, 1H), 7.26–7.36 (m, 3H), 7.22 (br t, 1H), 7.09 (d, 2H), 7.02 (d, 2H), 2.60–2.69 (m, 2H), 2.57–2.60 (m, 2H), 2.23 (s, 3H), 1.75–1.76 (m, 2H, and 1.46–1.53 ppm (m, 4H); IR (KBr) 3400 (br) cm$^{-1}$; negative FAB MS m/e 411 (M-Na). Anal. Calcd for C$_{24}$H$_{24}$N$_7$Na.H$_2$O: C, 63.84; H, 5.80; N, 21.72. Found: C, 63.90; H, 5.71; N, 21.47.

EXAMPLE 10

The preparation of N-[[2'-(1H-tetrazol-5-yl)[1,1'-biphenyl]-4-yl]methyl]-N-[2-(trifluoromethyl)-5,6,7,8-tetrahydro-quinazolin-4-yl]-glycine methyl ester To a 0° C. solution of 0.01 mmol of 5,6,7,8-tetrahydro-N-[[2'-(1H-tetrazol-5-yl)[1,1'-biphenyl]-4-yl]methyl]-2-(trifluoromethyl)-4-quinazolinamine in 10 mL of anhydrous DMF was added 0.01 mmol of NaH. The resulting solution was stirred at 0° C. for 30 minutes at which time 0.01 mmol of triphenylmethylchloride was added. The reaction mixture was stirred at room temperature for 18 hours and 0.01 mmol of methyl bromoacetate was added. After 24 hours the reaction mixture was diluted with water and extracted with ethyl acetate (3×10 mL). The organic phase was extracted with brine, dried over anhydrous magnesium sulfate, filtered and evaporated to yield a residue which was treated with 2N HCl in dioxane. The solvents were evaporated and the resulting residue was purified on silica to yield the title compound.

EXAMPLE 11

The preparation of N-[[2'-(1H-tetrazol-5-yl)[1,1'-biphenyl]-4-yl]methyl]-N-[2-(trifluoromethyl)-5,6,7,8-tetrahydro-quinazolin-4-yl]-glycine N-[4-[(5,6,7,8-Tetrahydro-2-(trifluoromethyl)-]quinazolinyl]-N-[[2'-(1H-tetrazol-5-yl)[1,1'-biphenyl]-4-yl]methyl]-2-glycine methyl ester (0.01 mmol) was dissolved in 20 mL of dioxane and 20 mL of 1.0N aqueous sodium hydroxide was added. The reaction was stirred at room temperature for 24 hours at which time the reaction mixture was adjusted to pH=4 with 1.0N HCl. the resulting residue was collected by filtration and was purified on silica to yield the title compound.

The following examples were or can be prepared using the procedures described in examples 10 and 11.

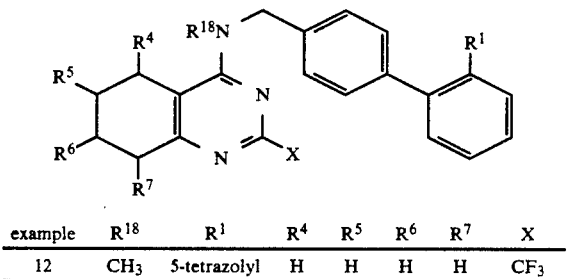

| example | $R^{18}$ | $R^1$ | $R^4$ | $R^5$ | $R^6$ | $R^7$ | X |
|---|---|---|---|---|---|---|---|
| 12 | CH$_3$ | 5-tetrazolyl | H | H | H | H | CF$_3$ |

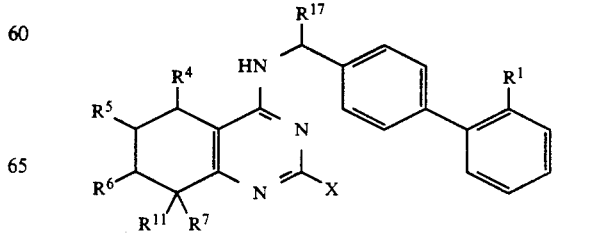

-continued

| example | R17 | R1 | R4 | R5 | R6 | R7 | R11 | X |
|---|---|---|---|---|---|---|---|---|
| 24 | —CO2Me | 5-tetrazolyl | H | H | H | H | H | CF3 |
| 25 | —CO2H | 5-tetrazolyl | H | H | H | H | H | CF3 |

Example 13

The preparation of
5-(acetyloxy)-5,6,7,8,-tetrahydro-N-[[2'-(1H-tetrazol-5-yl)[1,1'-biphenyl]4-yl]methyl]-2-(trifluoromethyl)-4-quinazolinamine Part A The preparation of
5-bromo-4-chloro-5,6,7,8-tetrahydro-2-trifluoromethyl-quinazoline To a solution of 17.63 g of 4-chloro-5,6,7,8,-tetrahydro-2-trifluoromethylquinazoline in 220 mL of chloroform was added 14.6 g of N-bromosuccinimide and 0.85 g of AIBN. The resulting reaction mixture was heated to reflux overnight under a nitrogen atmosphere. The reaction was cooled, filtered and all solvents were removed by evaporation. The residue was purified on a silica column (5% ethyl acetate in hexane) to yield 13.7 g (58%) of the required compound. This material was carried to the next step with no further purification.

Part B

The preparation of
5-(acetyloxy)-5,6,7,8-tetrahydro-N-[[2'-(1H-tetrazol-5-yl)[1,1'-biphenyl]-4-yl]methyl]-2-(trifluoromethyl)-4-quinazolinamine To 25 mL of DMSO was added 4.5 g of 5-bromo-4-chloro-5,6,7,8-tetrahydro-2-trifluoromethylquinazoline and 4.7 g of anhydrous sodium acetate. The reaction mixture was warmed for 2 hours at which time 4.1 g of N-[[2'-(1H-tetrazol-5-yl)[1,1'-biphenyl]-4-yl]methyl]amine hydrochloride was added and the reaction was heated to 40° C. overnight. The crude reaction mixture was purified on silica gel (20% methanol/chloroform) to yield the title product (1.9 g, 24%); $^1$H NMR (DMSO-d$_6$, 400 MHz) δ 7.78 (m, 1H), 7.63 (m, 2H), 7.53 (m, 2H), 7.24 (m, 2H); 7.03 (m, 2H), 5.64 (m, 1H), 4.52 (m,2H), 2.68 (m, 2H), 2.23 (m, 1H), 1.97 (s, 3H), 1.80 (m, 3H); positive DCI MS m/e 510 (M+H). Anal. calcd for C$_{25}$H$_{22}$F$_3$N$_7$O$_2$: C, 58.94; H, 4.35; N, 19.24. Found: C, 58.31; H, 4.30; N, 19.20.

EXAMPLE 16

The preparation of
5,6,7,8-tetrahydro-4-[[[2'-(1H-tetrazol-5-yl)[1,1'-biphenyl]-4-yl]methyl]amino]-2-(trifluoromethyl)-5-quinazolinol dihydrate To 25 mL of DMSO was added 4.5 g of 5-bromo-4-chloro-5,6,7,8-tetrahydro-2-trifluoromethylquinazoline and 4.7 g of anhydrous sodium acetate. The reaction mixture was warmed for 2 hours at which time 4.1 g of N-[[2'-(1H-tetrazol-5-yl)[1,1'-biphenyl]-4-yl]methyl]amine hydrochloride was added and the reaction was heated to 40° C. overnight. To the crude reaction mixture was added 24 mL of 2.5N aqueous sodium hydroxide. After 1 hour the reaction was diluted with 500 mL of water and was acidified with hydrochloric acid. The acidified reaction mixture was extracted with ethyl acetate and the organic fractions were washed with brine, dried over anhydrous magnesium sulfate, filtered and evaporated. The resulting residue was purified on silica to yield 5.3 g of the title product: $^1$H NMR (DMSO-d$_6$, 400 MHz) δ 7.80 (m, 1H), 7.60 (m, 2H), 7.48 (m, 2H), 7.28 (m, 2H), 7.03 (m, 2H), 5.33 (bs, 1H), 4.63 (m, 3H), 2.60 (m, 3H), 1.80 (m, 3H); positive DCI MS m/e 468(M+H); 506(M+K). Anal. calc'd for C$_{23}$H$_{20}$F$_3$N$_7$O.2H$_2$O: C, 54.87; H, 4.80; N, 19.48. Found: C, 54.52; H, 4.44; N, 18.14.

EXAMPLE 21

The preparation of
7,8-dihydro-4-[[2'-(1H-tetrazol-5-yl)[1,1'-biphenyl]-4-yl]methyl]amino]5(6H)-quinazolinone To a solution of 5,6,7,8-tetrahydro-4-[[[2'-(1H-tetrazol-5-yl)[1,1'-biphenyl]-4-yl]methyl]amino]-2-(trifluoromethyl)-5-quinazolinol (5.3 g) in 50 mL of wet acetone was added excess Jone's reagent (20.8 mL of 1N solution). The reaction mixture was heated to reflux for 1 hour at which time the reaction was cooled and the solvents were removed by evaporation. The residue was partitioned between chloroform and brine. The organic layer was dried over anhydrous magnesium sulfate, filtered and evaporated. The residue was recrystalized from methylene chloride to yield 2.78 g of the title product: $^1$H NMR (DMSO-d$_6$, 400 MHz) δ 9.90 (m, 1H), 7.60 (m, 2H), 7.50 (m, 2H), 7.28 (m, 2H), 7.07 (m, 2H), 4.73 (d, J=6.2 Hz, 2H), 2.92 (m, 2H), 2.66 (m, 2H), 2.05 (m, 2H); negative FAB m/e 466(M+H); 488(M+Na). Anal. calc'd for C$_{23}$H$_{18}$F$_3$N$_7$O.2H$_2$O: C, 56.90; H,4.57; N, 20.20. Found: C, 56.67; H, 3.97; N, 21.02.

The following example was or can be prepared using the procedures described in examples 13, 16 or 21.

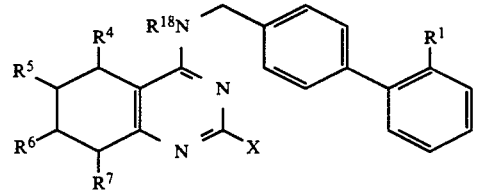

| example | R18 | R1 | R4 | R5 | R6 | R7 | X |
|---|---|---|---|---|---|---|---|
| 17 | H | 5-tetrazolyl | OMe | H | H | H | CF3 |

We claim:
1. The compounds of formula I:

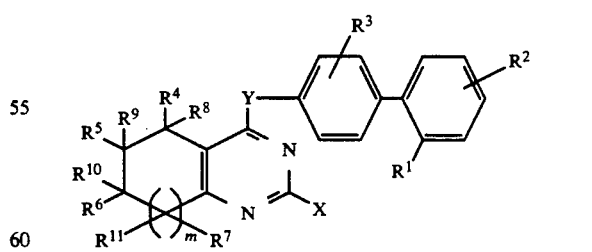

wherein
X is H, NR$^{12}$R$^{13}$, OR$^{14}$, CN, F, Cl, I, Br, perfluoroalkyl, alkyl, alkoxy, alkyl—OH, alkoxyalkyl, —(CH$_2$)$_n$CO$_2$R$^{14}$, —(CH$_2$)$_n$CONR$^{12}$R$^{13}$;
Y is NR$^{15}$, NR$^{18}$CR$^{16}$R$^{17}$, CR$^{16}$R$^{17}$NR$^{15}$;
R$^1$ is 5-tetrazolyl, CO$_2$R$^{14}$, SO$_3$H, NHSO$_2$CH$_3$, NHSO$_2$CF$_3$;

23

$R^2$, $R^3$ is H, alkyl, alkoxy, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$, $OR^{14}$, F, Cl, Br, I, $NR^{12}R^{13}$;

$R^4-R^{11}$ is H, F, alkyl, alkoxy, alkoxyalkyl, $-O-COR^{14}$, alkyl-OH, perfluoroalkyl, aralkyl, aryl, CN, $NO_2$, $SO_2R^{19}$, $-(CH_2)_nCO_2R^{14}$, $-(CH_2)_nCONR^{12}R^{13}$, OH, $OR^{14}$, $-NR^{12}R^{13}$, any two geminal groups can be O or $CH_2$;

$R^{12}$, $R^{13}$ is H, alkyl, aralkyl;

$R^{14}$ is H, alkyl, aralkyl, alkoxyalkyl;

$R^{15}$ is H, alkyl, $-(CH_2)_nCO_2R^{14}$, alkoxyalkyl, aralkyl, $-(CH_2)_nCONR^{12}R^{13}$, $OR^{14}$, perfluoroalkyl, alkyl—OH, $-COR^{14}$, $-CONR^{12}R^{13}$;

$R^{16}$, $R^{17}$ is H, alkyl, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$;

$R^{18}$ is H, alkoxyalkyl, alkyl—OH, perfluoroalkyl, aralkyl, $OR^{14}$, $-(CH_2)_nCO_2R^{14}$, $-(CH_2)_nCONR^{12}R^{13}$, alkyl, $-COR^{14}$, $-CONR^{12}R^{13}$;

$R^{19}$ is alkyl, aralkyl;

n is 0, 1, 2 or 3;

m is 1–5 and the pharmaceutically acceptable salts, solvates and hydrates thereof.

2. The compounds of claim 1 wherein

X is H, CN, F, Cl, I, Br, perfluoroalkyl, alkyl, alkoxy, alkyl—OH, alkoxyalkyl, $-(CH_2)_nCO_2R^{14}$, $-(CH_2)_nCONR^{12}R^{13}$;

Y is $NR^{15}$, $-NR^{18}CR^{16}R^{17}$, $-CR^{16}R^{17}NR^{15}$;

$R^1$ is 5-tetrazolyl, $-CO_2H$, $SO_3H$, $NHSO_2CF_3$;

$R^2$, $R^3$ is H, alkyl, alkoxy, alkoxyalkyl, alkyl—OH, perfluoroalkyl, aralkyl, CN, $NO_2$, $SO_2R^{19}$, $-(CH_2)_nCO_2R^{14}$, $-(CH_2)_nCONR^{12}R^{13}$, $OR^{14}$, F, Cl, Br, I, $NR^{12}R^{13}$;

$R^4-R^{11}$ is H, F, alkyl, alkoxy, alkoxyalkyl, $OCOR^{14}$, alkyl-OH, perfluoroalkyl, aralkyl, aryl, CN, $NO_2$, $SO_2R^{19}$, $-(CH_2)_nCO_2R^{14}$, $-(CH_2)_nCONR^{12}R^{13}$, OH, $OR^{14}$, $NR^{12}R^{13}$, any two geminal group can be O or $CH_2$;

$R^{12}$, $R^{13}$ is H, alkyl, aralkyl;

$R^{14}$ is H, alkyl, aralkyl, alkoxyalkyl;

$R^{15}$ is H, alkyl, $-(CH_2)_nCO_2R^{14}$, alkoxyalkyl, aralkyl, $-(CH_2)_nCONR^{12}R^{13}$, $OR^{14}$, perfluoroalkyl, alkyl—OH, $-COR^{14}$, $-CONR^{12}R^{13}$;

$R^{16}$, $R^{17}$ is H, alkyl, alkoxyalkyl, alkyl-OH, perfluoroalkyl, aralkyl, CN, $NO_2$, $SO_2R^{19}$, $-(CH_2)_nCO_2R^{14}$, $-(CH_2)_nCONR^{12}R^{13}$;

$R^{18}$ is H, alkoxyalkyl, alkyl-OH, perfluoroalkyl, aralkyl, $OR^{14}$, $-(CH_2)_nCO_2R^{14}$, $-(CH_2)_nCONR^{12}R^{13}$, alkyl, $-COR^{14}$, $-CONR^{12}R^{13}$;

$R^{19}$ is alkyl, aralkyl;

n is 0, 1, 2 or 3;

m is 1, 2, 3 and the pharmaceutically acceptable salts, solvates and hydrates thereof.

3. The compounds of claim 2 wherein

X is perfluoroalkyl, alkyl, alkoxy, alkyl-OH;

Y is $-NR^{18}CR^{16}R^{17}$, $-CR^{16}R^{17}NR^{15}$;

$R^1$ is 5-tetrazolyl, $-CO_2H$, $SO_3H$, $NHSO_2CF_3$;

$R^2$, $R^3$ is H, alkyl, alkoxy, alkoxyalkyl, alkyl-OH, perfluoroalkyl, $-CN$, $NO_2$, $-(CH_2)_nCO_2R^{14}$, $-(CH_2)_nCONR^{12}R^{13}$, $OR^{14}$, F, Cl, Br, $NR^{12}R^{13}$;

$R^4-R^{11}$ is H, F, alkyl, alkoxy, alkoxyalkyl, $OCOR^{14}$, alkyl-OH, perfluoroalkyl, aralkyl, CN, $-(CH_2)_nCO_2R^{14}$, $-(CH_2)_nCONR^{12}R^{13}$, OH, $OR^{14}$, $NR^{12}R^{13}$, any two geminal groups can be O or $CH_2$;

$R^{12}$, $R^{13}$ is H, alkyl, aralkyl;

$R^{14}$ is H, alkyl, aralkyl, alkoxyalkyl;

24

$R^{15}$ is H, alkyl, $-(CH_2)_nCO_2$alkyl, $-(CH_2)_nCO_2H$, $-CO$alkyl, $-COH$;

$R^{16}$, $R^{17}$ is H, $-CO_2H$, $-CO_2$alkyl;

$R^{18}$ is H, alkyl, $-(CH_2)_nCO_2$alkyl, $-(CH_2)_nCO_2H$, $-CO$alkyl, $-COH$;

n is 0, 1, 2;

m is 1, 2, 3 and the pharmaceutically acceptable salts, solvates and hydrates thereof.

4. The compounds of claim 3 wherein

X is $-CF_3$, $-CH_3$, $-iPr$;

Y is $-NR^{18}CR^{16}R^{17}$;

$R^1$ is 5-tetrazolyl, $-CO_2H$;

$R^2$, $R^3$ is H, F;

$R^4-R^{11}$ is F, alkyl, $-OCOR^{14}$, perfluoroalkyl, $-OH$, Oalkyl, any two geminal groups can be O;

$R^{14}$ is alkyl;

$R^{16}$, $R^{17}$ is H, $-CO_2H$, $-CO_2CH_3$;

$R^{18}$ is H, alkyl, $-CH_2CO_2CH_3$, $-CO_2H$;

n is 0, 1;

m is 1, 2, 3 and the pharmaceutically acceptable salts, solvates and hydrates thereof.

5. The compound of claim 4: 4'-[[[5,6,7,8-tetrahydro-2-(trifluoromethyl)-4-quinazolinyl]amino]methyl][1,1'-biphenyl]-2-carboxylic acid and the pharmaceutically acceptable salts, solvates and hydrates thereof.

6. The compound of claim 4: 5,6,7,8-tetrahydro-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

7. The compound of claim 4: 5,6,7,8-tetrahydro-2-methyl-N-[[2'-(1H-tetrazol-5-yl)[1,1'-biphenyl]-4-yl]methyl]-4-quinazolinamine and the pharmaceutically acceptable salts, solvates and hydrates thereof.

8. The compound of claim 4: 7-methyl-5,6,7,8-tetrahydro-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

9. The compound of claim 4: 4'-[[(5,6,7,8-tetrahydro-2-methyl-4-quinazolinyl)amino]methyl][1,1'-biphenyl]-2-carboxylic acid and the pharmaceutically acceptable salts, solvates and hydrates thereof.

10. The compound of claim 4: 5,6,7,8,-tetrahydro-N-methyl-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

11. The compound of claim 4: 5-(acetyloxy)-5,6,7,8,-tetrahydro-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

12. The compound of claim 4: 5,6,7,8-tetrahydro-2-(1-methylethyl)-N-[[2'-(1H-tetrazol-5-yl)[1,1'-biphenyl]-4-yl]methyl]-4-quinazolinamine and the pharmaceutically acceptable salts, solvates and hydrates thereof.

13. The compound of claim 4: 5,6,7,8-tetrahydro-8-methyl-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

14. The compound of claim 4: 5,6,7,8-tetrahydro-4-[[[2'-(1H-tetrazol-5-yl)[1,1'-biphenyl]-4-yl]methyl]amino]-2-(trifluoromethyl)-5-quinazolinol and the pharmaceutically acceptable salts, solvates and hydrates thereof.

15. The compound of claim 4: 5,6,7,8-tetrahydro-5-methoxy-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

16. The compound of claim 4: 3'-fluoro-4'-[[(5,6,7,8-tetrahydro-2-methyl-4-quinazolinyl)amino]methyl][1,1'-biphenyl]-2-carboxylic acid and the pharmaceutically acceptable salts, solvates and hydrates thereof.

17. The compound of claim 4: N-[[3-fluoro-2'-(1H-tetrazol-5-yl)[1,1'-biphenyl]-4-yl]methyl]-5,6,7,8,-tetrahydro-2-(trifluoromethyl)-4-quinazolinamine and the pharmaceutically acceptable salts, solvates and hydrates thereof.

18. The compound of claim 4: N-[[3-fluoro-2'-(1H-tetrazol-5-yl)[1,1'-biphenyl]-4-yl]methyl]-5,6,7,8-tetrahydro-2-methyl-4-quinazolinamine and the pharmaceutically acceptable salts, solvates and hydrates thereof.

19. The compound of claim 4: 8,8-difluoro-5,6,7,8-tetrahydro-N-[[2'-(1H-tetrazol-5-yl)[1,1'-biphenyl]-4-yl]methyl]-2-(trifluoromethyl)-4-quinazolinamine and the pharmaceutically acceptable salts, solvates and hydrates thereof.

20. The compound of claim 4: 7,8-dihydro-4-[[2'-(1H-tetrazol-5-yl)[1,1'-biphenyl-4-yl]methyl]amino]5(6H)-quinazolinone and the pharmaceutically acceptable salts, solvates and hydrates thereof.

21. The compound of claim 4: 4'-[[[6,7,8,9, -tetrahydro-2-(trifluoromethyl)-5H-cycloheptapyrimidin-4-yl]amino]methyl][1,1'-biphenyl]-2-carboxylic acid and the pharmaceutically acceptable salts, solvates and hydrates thereof.

22. The compound of claim 4: 6,7,8,9,-tetrahydro-N-[[2'-(1H-tetrazol-5-yl) [1,1'-biphenyl]-4-yl]methyl]-2-(trifluoromethyl)-5H-cycloheptapyrimidin-4-amine and the pharmaceutically acceptable salts, solvates and hydrates thereof.

23. The compound of claim 4: 6,7,8,9-tetrahydro-2-methyl-N-[[2'-(1H-tetrazol-5-yl)[1,1'-biphenyl]-4-yl]methyl]-5H-cycloheptapyrimidin-4-amine and the pharmaceutically acceptable salts, solvates and hydrates thereof.

24. The compound of claim 4: 5,6,7,8,9,10-hexahydro-N-[[2'-(1H-tetrazol-5-yl) [1,1'-biphenyl]-4-yl]methyl]-2-(trifluoromethyl)-4-cyclooctapyrimidinamine and the pharmaceutically acceptable salts, solvates and hydrates thereof.

25. The compound of claim 4: 5,6,7,8,9,10-hexahydro-2-methyl-N-[[2'-(1H-tetrazol-5-yl)[1,1'-biphenyl]-4-yl]methyl]-4-cyclooctapyrimidinamine and the pharmaceutically acceptable salts, solvates and hydrates thereof.

26. The compound of claim 4: N-[[2'-(1H-tetrazol-5-yl)[1,1'-biphenyl]-4-yl]methyl]-N-[2-(trifluoromethyl)-5,6,7,8-tetrahydro-quinazolin-4-yl]-glycine methyl ester and the pharmaceutically acceptable salts, solvates and hydrates thereof.

27. The compound of claim 4: N-[[2'-(1H-tetrazol-5-yl)[1,1'-biphenyl]-4-yl]-methyl]-N-[2-(trifluoromethyl)-5,6,7,8-tetrahydro-quinazolin-4-yl]-glycine and the pharmaceutically acceptable salts, solvates and hydrates thereof.

28. The compound of claim 4: [2'-(1H-tetrazol-5-yl)[1,1'-biphenyl]-4-yl]-[2-(trifluoromethyl)-5,6,7,8-tetrahydro-quinazolin-4-ylamino]-acetic acid methyl ester and the pharmaceutically acceptable salts, solvates and hydrates thereof.

29. The compound of claim 4: [2'-(1H-tetrazol-5-yl)[1,1'-biphenyl]-4-yl]-[2-(trifluoromethyl)-5,6,7,8-tetrahydro-quinazolin-4-ylamino]-acetic acid and the pharmaceutically acceptable salts, solvates and hydrates thereof.

30. A pharmaceutical composition containing a compound of claim 1, in an amount effective for producing a hypotensive response in a mammal, and a pharmaceutically acceptable carrier, vehicle or diluent.

* * * * *